(12) United States Patent
Trieu

(10) Patent No.: US 11,717,422 B2
(45) Date of Patent: Aug. 8, 2023

(54) SPINAL IMPLANT SYSTEM AND METHOD

(71) Applicant: WARSAW ORTHOPEDIC INC., Warsaw, IN (US)

(72) Inventor: Hai H. Trieu, Cordova, TN (US)

(73) Assignee: Warsaw Orthopedic Inc., Warsaw, IN (US)

( * ) Notice: Subject to any disclaimer, the term of this patent is extended or adjusted under 35 U.S.C. 154(b) by 167 days.

(21) Appl. No.: 17/320,441

(22) Filed: May 14, 2021

(65) Prior Publication Data

US 2021/0267772 A1 Sep. 2, 2021

Related U.S. Application Data

(60) Division of application No. 16/538,264, filed on Aug. 12, 2019, now Pat. No. 11,026,813, which is a
(Continued)

(51) Int. Cl.
 *A61F 2/44* (2006.01)
 *A61F 2/46* (2006.01)
 *A61F 2/30* (2006.01)

(52) U.S. Cl.
 CPC ........ *A61F 2/4637* (2013.01); *A61F 2/30942* (2013.01); *A61F 2/447* (2013.01); *A61F 2/4455* (2013.01); *A61F 2/4611* (2013.01); *A61F 2002/305* (2013.01); *A61F 2002/3092* (2013.01); *A61F 2002/3097* (2013.01); *A61F 2002/30448* (2013.01); *A61F 2002/30481* (2013.01); *A61F 2002/30593* (2013.01); *A61F 2002/30607* (2013.01); *A61F 2002/30616* (2013.01); *A61F 2002/30828* (2013.01);
(Continued)

(58) Field of Classification Search
 CPC .. A61F 2/442–4425; A61F 2/4455–447; A61F 2/4611; A61F 2/4637; A61F 2220/0033
 See application file for complete search history.

(56) References Cited

U.S. PATENT DOCUMENTS 7,419,505 B2 * 9/2008 Fleischmann ......... A61F 2/4611
 623/17.11
8,133,282 B2 3/2012 Hushka et al.
(Continued)

OTHER PUBLICATIONS

Examination report No. 1 for standard patent application, Australian Patent Office, Application No. 2020202313 Applicant name Warsaw Orthopedic, Inc., dated Jul. 30, 2020.
(Continued)

*Primary Examiner* — Eduardo C Robert
*Assistant Examiner* — Steven J Cotroneo
(74) *Attorney, Agent, or Firm* — Sorell, Lenna & Schmidt, LLP

(57) ABSTRACT

A spinal implant system includes at least one interbody implant having a first member including a tissue engaging surface and at least one mating element. A second member includes a tissue engaging surface and at least one mating element. An intermediate member includes at least one mating element. An intra-operative surgical tool is connectable with at least one of the members to engage adjacent mating elements and fix the intermediate member with at least one of the first member and the second member. Implants, surgical instruments and methods are disclosed.

16 Claims, 11 Drawing Sheets

Related U.S. Application Data continuation of application No. 14/663,193, filed on Mar. 19, 2015, now Pat. No. 10,413,427.

(52) U.S. Cl.
CPC ............... *A61F 2002/30904* (2013.01); *A61F 2002/30968* (2013.01); *A61F 2002/30971* (2013.01); *A61F 2002/30973* (2013.01); *A61F 2002/30985* (2013.01); *A61F 2220/0033* (2013.01)

(56) References Cited

U.S. PATENT DOCUMENTS

| | | | | |
|---|---|---|---|---|
| 8,303,879 | B2* | 11/2012 | Bertele | A61F 2/30907 |
| | | | | 264/273 |
| 8,353,964 | B2* | 1/2013 | Carpenter | A61F 2/4611 |
| | | | | 623/17.16 |
| 8,414,650 | B2 | 4/2013 | Bertele et al. | |
| 8,414,820 | B2 | 4/2013 | Bertele et al. | |
| 8,425,604 | B2 | 4/2013 | Trieu | |
| 8,562,685 | B2* | 10/2013 | Ullrich, Jr. | A61F 2/442 |
| | | | | 623/17.11 |
| 8,645,563 | B2 | 2/2014 | Riley et al. | |
| 2002/0010473 | A1* | 1/2002 | Lin | A61B 17/025 |
| | | | | 606/99 |
| 2002/0116009 | A1* | 8/2002 | Fraser | A61B 17/025 |
| | | | | 606/99 |
| 2002/0161375 | A1* | 10/2002 | Ralph | A61F 2/4611 |
| | | | | 606/99 |
| 2003/0187506 | A1* | 10/2003 | Ross | A61F 2/4465 |
| | | | | 623/17.13 |
| 2003/0225416 | A1* | 12/2003 | Bonvallet | A61B 17/025 |
| | | | | 606/205 |
| 2003/0229355 | A1* | 12/2003 | Keller | A61F 2/4611 |
| | | | | 606/247 |
| 2005/0096744 | A1* | 5/2005 | Trieu | A61F 2/4611 |
| | | | | 623/17.11 |
| 2006/0200244 | A1* | 9/2006 | Assaker | A61F 2/44 |
| | | | | 623/17.15 |
| 2006/0287728 | A1* | 12/2006 | Mokhtar | A61F 2/4425 |
| | | | | 606/90 |
| 2007/0043442 | A1* | 2/2007 | Abernathie | A61F 2/4455 |
| | | | | 623/17.11 |
| 2007/0093900 | A1* | 4/2007 | Williams | A61F 2/4455 |
| | | | | 623/17.11 |
| 2007/0118221 | A1* | 5/2007 | Robie | A61L 27/08 |
| | | | | 623/17.11 |
| 2007/0123904 | A1* | 5/2007 | Stad | A61F 2/4611 |
| | | | | 606/99 |
| 2008/0161928 | A1* | 7/2008 | Trieu | A61F 2/442 |
| | | | | 606/151 |
| 2012/0191190 | A1* | 7/2012 | Trieu | A61F 2/442 |
| | | | | 623/17.11 |
| 2012/0209384 | A1 | 8/2012 | Arnold et al. | |
| 2012/0265303 | A1* | 10/2012 | Refai | A61F 2/4465 |
| | | | | 623/17.11 |
| 2012/0312778 | A1* | 12/2012 | Ullrich, Jr. | C23C 14/34 |
| | | | | 451/28 |

OTHER PUBLICATIONS

Examination report No. 1 for standard patent application, Australian Patent Office, 2016233759, dated Sep. 23, 2019.

\* cited by examiner

SPINAL IMPLANT SYSTEM AND METHOD

CROSS REFERENCE TO RELATED APPLICATIONS

This application is a divisional of U.S. patent application Ser. No. 16/538,264, filed on Aug. 12, 2019, which is a continuation of U.S. patent application Ser. No. 14/663,193, filed on Mar. 19, 2015, now U.S. Pat. No. 10,413,427. These applications are hereby expressly incorporated herein by reference, in their entireties.

TECHNICAL FIELD

The present disclosure generally relates to medical devices for the treatment of musculoskeletal disorders, and more particularly to a surgical system and method for treating a spine.

BACKGROUND

Spinal pathologies and disorders such as degenerative disc disease, disc herniation, osteoporosis, spondylolisthesis, stenosis, tumor, scoliosis and other curvature abnormalities, kyphosis and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, partial or complete discectomy, corpectomy and laminectomy, and implantable prosthetics. As part of these surgical treatments, spinal constructs, such as, for example, bone fasteners, spinal rods and interbody devices can be used to provide stability to a treated region. For example, during surgical treatment, interbody implants can be delivered to a surgical site for fixation with bone to immobilize a joint. This disclosure describes an improvement over these technologies.

SUMMARY

In one embodiment, a spinal implant system is provided. The spinal implant system includes at least one interbody implant that comprises a first member including a tissue engaging surface and at least one mating element. A second member includes a tissue engaging surface and at least one mating element. An intermediate member includes at least one mating element. An intra-operative surgical tool is connectable with at least one of the members to engage adjacent mating elements and fix the intermediate member with at least one of the first member and the second member. In some embodiments, implants, surgical instruments and methods are provided.

BRIEF DESCRIPTION OF THE DRAWINGS

The present disclosure will become more readily apparent from the specific description accompanied by the following drawings, in which.

DETAILED DESCRIPTION

Figure 1:
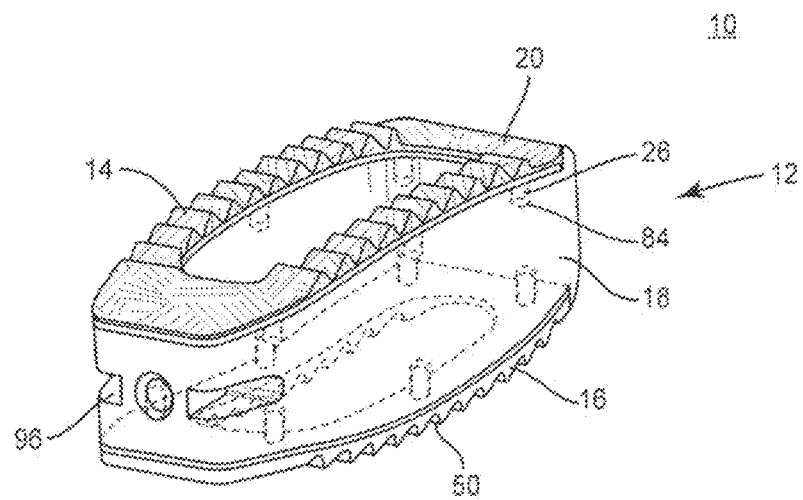
FIG. 1 is a perspective view of components of one embodiment of a surgical system in accordance with the principles of the present disclosure.
Figure 2:
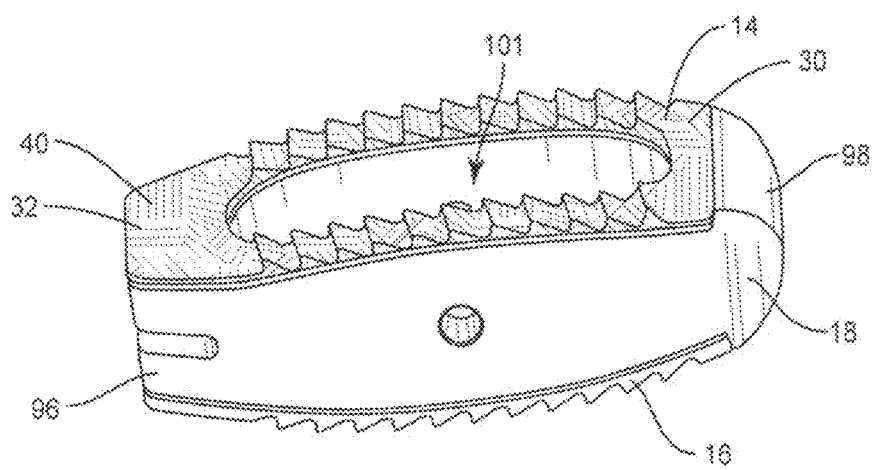
FIG. 2 is a perspective view of the components shown in FIG. 1.
Figure 3:
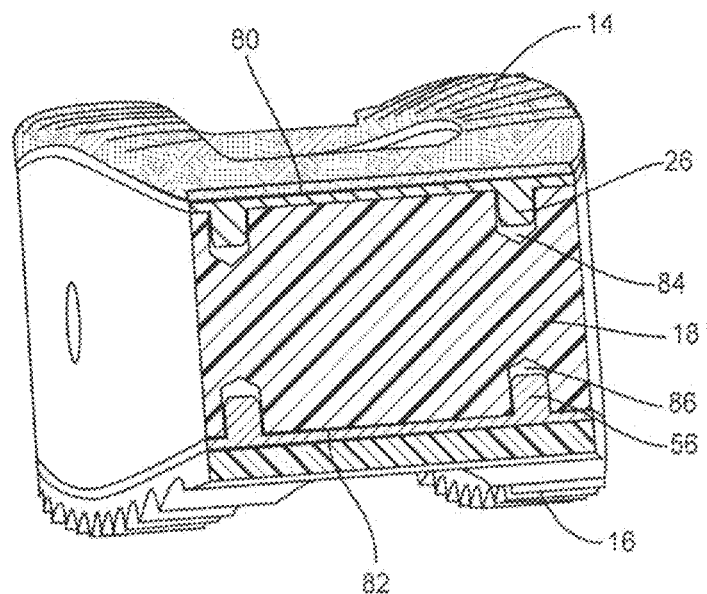
FIG. 3 is a cutaway perspective view of the components shown in FIG. 1.

The exemplary embodiments of the surgical system and related methods of use disclosed are discussed in terms of medical devices for the treatment of musculoskeletal disorders and more particularly, in terms of a surgical system including a spinal implant and a method for treating a spine. In one embodiment, the systems and methods of the present disclosure are employed with a spinal joint fusion, for example, with a cervical, thoracic, lumbar and/or sacral region of a spine.

In some embodiments, the present system includes one or more osseo-integration implants. In some embodiments, the present system is employed with a method that includes intra-operative assembly of osseo-integration implants. In some embodiments, the present system includes one or more personalized osseo-integration implants. In some embodiments, the present system is employed with a method that includes intra-operative assembly of personalized osseo-integration implants. In some embodiments, the present system is employed with a method that includes intra-operative assembly of hybrid titanium-polyetheretherketone (PEEK) osseo-integration implants.

In some embodiments, the present system includes a surgical spinal implant kit having one or more spinal implants, which include components, such as, for example, one or more endplates and a substrate body. In some embodiments, the spinal implant kit includes specialized and sterilized and/or non-sterilized packed tools configured for crimping or pressing the components of the spinal implant. In some embodiments, the spinal implant kit is employed with a method for on-site assembly of selectable printed and/or osseo-integrative titanium endplates that may or may not be coated. In some embodiments, the spinal implant includes an interbody device.

In some embodiments, the endplates have engaging surfaces. In some embodiments, the spinal implant includes a pair of endplates. In some embodiments, the endplates include metal or ceramic material. In some embodiments, the endplates include attachment, engagement or securing elements on engaging surfaces. In some embodiments, the endplates includes a titanium surface. In some embodiments, the engaging surfaces include pins.

In some embodiments, the present system includes a spinal implant having a polymer substrate with attachment, engagement and/or securing elements. In some embodiments, the polymer substrate includes a PEEK middle component with holes on engaging surfaces. In some embodiments, the spinal implant includes a pair of metal or ceramic endplates with corresponding attachment, engagement or securing elements. In some embodiments, the endplates include titanium surface endplates with pins on engaging surfaces.

In some embodiments, the endplates are made from biocompatible materials, such as, for example, titanium, titanium alloys, Nitinol, tantalum, cobalt-chrome alloys, stainless steel, silicon nitride, hydroxyapatite (HA), coralline HA, calcium phosphate (CP), calcium sulfate, bioactive glasses, or their composites or combinations. In some embodiments, the endplates are made from a porous titanium coated with a thin HA layer, porous titanium endplates filled with HA or CP.

In some embodiments, the present system includes endplates fabricated or produced via methods of manufacturing, such as, for example, machining, injection molding, compression molding, casting, sintering, additive manufacturing or 3D-printing or laser sintering, or their combinations. In some embodiments, the present system includes metallic and/or ceramic endplates fabricated or produced at locations, such as, for example, a manufacturer's production facilities, manufacturer's global or local distribution centers, hospitals, outpatient surgery centers and/or operating rooms. In some embodiments, the methods of manufacturing can include machining, molding, casting and/or sintering. In some embodiments, the methods of manufacturing include additive manufacturing, 3D-printing or laser sintering with smaller and automated equipment at local distribution facilities, hospitals, outpatient surgery centers and/or operating rooms. In some embodiments, methods of manufacturing components of the present system can include secondary operations to prepare the endplates. In some embodiments, the secondary operations include trimming, machining, removing support materials (for additive manufacturing or 3D printing), surface finishing, polishing, cleaning, decontamination and/or sterilization.

In some embodiments, the present system includes a polymer substrate having attachment, engagement or securing elements, such as, for example holes. In some embodiments, the polymer substrate includes polymeric biomaterials, such as, for example, PEEK, polyetherketoneketone (PEKK), members of the polyaryletherketone (PAEK) family, composites of members of the PAEK family with carbon fibers, hydroxyapatite whiskers or particles, bioactive glass particles or whiskers, particles or fibers of titanium or titanium alloys and/or barium sulfate particles. Other polymers include polyethylene, polypropylene, polyurethane, polyester and/or polysulfone. In some embodiments, the substrate can be manufactured from ceramic materials that may include silicon nitride, alumina, zirconia, HA and/or bioactive glasses.

In some embodiments, the polymer substrate can be fabricated or produced via methods of manufacturing including machining, injection molding, compression molding, casting, additive manufacturing or 3D-printing, or their combinations. In some embodiments, the polymer substrate can be fabricated or produced at locations, such as, for example, manufacturer's production facilities, manufacturer's global or local distribution centers, hospitals, outpatient surgery centers and/or operating rooms. In some embodiments, components of the present system can be fabricated or produced via methods of manufacturing including additive manufacturing or 3D-printing with smaller and more automated equipment at local distribution facilities, hospitals, outpatient surgery centers and/or operating rooms.

In some embodiments, methods of manufacturing components of the present system can include secondary operations to prepare the polymer substrate. In some embodiments, the secondary operations include trimming, machining, removing support materials (for additive manufacturing or 3D printing), surface finishing, polishing, cleaning, decontamination and/or sterilization.

In some embodiments, the present system includes one or more surgical tools configured to facilitate assembly of a spinal implant, which includes one or more endplates and a polymer substrate. In some embodiments, the present system includes a surgical tool configured to facilitate assembly of the endplates to the polymer substrate. In some embodiments, the surgical tool includes a hand press. In some embodiments, the surgical tool includes a table-top press. In some embodiments, the surgical tool includes an ultrasonic welding press. In some embodiments, the present system includes one or more of the components provided in sterile packaging. In some embodiments, the present system includes non-sterile components being compatible with a sterilization process in clinical settings. In some embodiments, the method includes the step of attaching the endplates and the substrate by attachment of both endplates to the substrate simultaneously. In some embodiments, the method includes the step of attaching the endplates and the substrate by attachment of a first endplate to the substrate and then attachment of a second endplate to the substrate.

In some embodiments, the surgical tool includes cavities and/or slots for capturing the endplates and the substrate. In some embodiments, the surgical tool includes an automatic alignment element for aligned attachment or engagement of the endplates with the substrate. In some embodiments, the surgical tool includes an element for protection of the endplates and the substrate to resist and/or prevent damage during contact and under pressure. In some embodiments, the surgical tool includes operator leverage to apply pressure to the components of the present system for attachment and engagement. In some embodiments, the surgical tool includes indicia and/or an indicator to protect from under and over-pressing during assembly. In some embodiments, the surgical tool includes heating, cooling, ultrasonic welding, disassembly, manual or power/automatic operation of one or more steps, adjustable tool accommodating various implant sizes, alternately interchangeable inserts to accommodate different sizes of implant in foot-print, angulation and/or height variations.

In some embodiments, the present system includes a surgical tool utilized to assemble the spinal implants prior to or during a surgical procedure inside or outside a clinical setting. In some embodiments, the surgical tool can be sterilized and re-sterilized in a clinical setting. In some embodiments, the surgical tool can be provided as a sterile disposable item. In some embodiments, the surgical tool may be used to disassemble the implant. In some embodiments, the surgical tool may be provided in a sterile package. In some embodiments, the surgical tool is provided in a non-sterile package and is compatible with sterilization process in clinical settings. In some embodiments, the surgical tool can be made of metal, polymer, ceramic, composite or their combinations. In some embodiments, the surgical tool can be handheld or table top. In some embodiments, the surgical tool may be manually operated or electrically powered. In some embodiments, the surgical tool is programmable and automated.

In some embodiments, the present system includes a surgical tool having a base configured to engage and align the components. In some embodiments, the surgical tool includes an actuator configured to apply force and/or pressure such that the endplates engage the substrate. In some embodiments, the surgical tool may include two actuators configured to compress towards each other to apply a force and/or pressure. In some embodiments, the surgical tool includes a base and/or an actuator having cavities, slots, ridges, pins, guides and/or tabs for holding components of the present system and/or guiding alignment. In some embodiments, the holding and/or alignment features may be integral or separate from the actuator and/or base.

In some embodiments, the present system includes a non-sterile spinal implant kit that is employed with a surgical procedure for a one vertebral level bilateral posterior lumbar interbody fusion (PLIF). In some embodiments, the present system includes a spinal implant kit including at least two pairs of endplates, two sets of substrates with a range of heights for selection and a reusable surgical tool employed with a method to assemble the components. In some embodiments, the present system includes components and a surgical tool that are sterilized prior to surgery.

In some embodiments, the present system is employed with a method that includes a step of measuring a disc height to determine an implant height and then selecting a substrate height. In some embodiments, the present system includes two endplates and one substrate that are employed with a method to assemble one spinal implant. In some embodiments, the present system is employed with a method that includes two implants assembled using a surgical tool for a PLIF at single vertebral level.

In some embodiments, the present system includes a sterile spinal implant kit that is employed with a surgical procedure for a one vertebral level bilateral transforaminal lumbar interbody fusion (TLIF). In some embodiments, the present system includes a spinal implant kit having at least two pairs of endplates in sterile packages, two sets of substrates in sterile packages having a range of heights for selection, and a disposable surgical tool employed with a method to assemble a spinal implant in a sterile package. In some embodiments, the present system is employed with a surgical procedure in an operating room.

In some embodiments, the present system is employed with a method that includes a step of measuring a disc height, determining an implant height and then selecting a substrate height. In some embodiments, the present system is employed with a method such that two endplates and one substrate are used to assemble one spinal implant. In some embodiments, the present system is employed with a method such that two implants are assembled using a surgical tool to assemble a spinal implant for a TLIF at single vertebral level.

In some embodiments, the present system includes a sterile spinal implant kit that is employed with a surgical procedure for a two vertebral level bilateral PLIF. In some embodiments, the present system includes a spinal implant kit having at least four pairs of endplates in sterile packages, four sets of substrates in sterile packages having a range of heights for selection, and a disposable surgical tool employed with a method for assembly of a spinal implant in a sterile package. In some embodiments, the present system is employed with a method that includes a step of measuring a disc height for each level, determining an implant height and then selecting a substrate height. In some embodiments, the present system is employed with a method such that two implants are assembled with a surgical tool for a PLIF at each of two vertebral levels.

In some embodiments, the present system includes a sterile spinal implant kit that is employed with a surgical procedure for a three vertebral level anterior cervical disc fusion (ACDF). In some embodiments, the present system includes a spinal implant kit having at least three pairs of endplates in sterile packages, three sets of substrates in sterile packages having a range of heights for selection, and a disposable surgical tool employed with a method for assembly in a sterile package. In some embodiments, the present system is employed with a method that includes a step of measuring a disc height for each level, determining an implant height and then selecting a substrate height. In some embodiments, the present system is employed with a method such that two endplates and one substrate are employed to assemble one spinal implant. In some embodiments, the present system is employed with a method such that three implants are assembled using a surgical tool for ACDF at three vertebral levels.

In some embodiments, the present system includes a sterile spinal implant kit that is employed with a surgical procedure for a one vertebral level direct lateral lumbar interbody fusion (DLIF). In some embodiments, the present system includes a spinal implant kit having at least one pair of endplates in sterile packages, one set of substrates in sterile packages having a range of heights for selection, and a disposable surgical tool employed with a method for assembly in a sterile package. In some embodiments, the present system is employed with a method that includes a step of measuring a disc height, determining an implant height and then selecting a substrate height. In some embodiments, the present system is employed with a method such that two endplates and one substrate are employed to assemble one spinal implant for a DLIF at a single vertebral level.

In some embodiments, the present system includes a spinal implant kit that is employed with a surgical procedure for a one vertebral level oblique lumbar interbody fusion (OLIF). In some embodiments, the present system includes a spinal implant kit having at least two pairs of endplates in sterile packages, one set of substrates in sterile packages with a full range of heights for selection, and a non-sterile reusable surgical tool employed with a method for assembly. In some embodiments, only the non-sterile reusable surgical tool is sterilized prior to surgery. In some embodiments, the present system is employed with a method that includes a step of measuring a disc height, determining an implant height and then selecting a substrate height. In some embodiments, the present system is employed with a method such that two endplates and one substrate are used to assemble one spinal implant for OLIF at a single vertebral level.

In some embodiments, the present system includes a partial sterile spinal implant kit that is employed with a surgical procedure for a one vertebral level OLIF. In some embodiments, the present system includes a spinal implant kit having at least one substrate in sterile packaging having a range of heights for selection, a surgical tool employed with a method for assembly in a sterile package without the endplates. In some embodiments, the present system is employed with a method that includes a step of, prior to surgery, fabricating a pair of matching endplates at the hospital or an outpatient surgery center using additive manufacturing equipment, as described herein, on site. In some embodiments, the method includes the steps of cleaning the endplates, and/or preparing and sterilizing the endplates before being used for the assembly of the spinal implant. In some embodiments, the present system is employed with a method that includes a step of measuring a disc height, determining an implant height and then selecting a substrate height. In some embodiments, the present system is employed with a method such that two endplates are fabricated on-site and a selected substrate are employed to assemble one spinal implant for an OLIF at a single vertebral level. In some embodiments, the present system includes a partial spinal implant kit such that the substrate is fabricated on site using additive manufacturing, as described herein.

In some embodiments, the present system includes a personalized and/or custom spinal implant kit assembled for a one vertebral level OLIF. In some embodiments, the present system is employed with a method such that, prior to surgery, a surgeon conducts pre-operative planning using x-ray, CT and/or MRI to measure disc height, predetermined implant size/height and preselects a size and/or height for endplates and a substrate. In some embodiments, the endplates and the substrate are fabricated at a hospital or an outpatient surgery center using additive manufacturing equipment on site.

In some embodiments, one or more components of the present system are cleaned, prepared and sterilized before being used for the assembly of a spinal implant. In some embodiments, a surgeon can confirm disc height and implant size and/or height during implantation. In some embodiments, two endplates and a substrate are fabricated on-site and are used to assemble one spinal implant for an OLIF at a single vertebral level. In some embodiments, the present system includes additional fabricated endplates and/or substrate of similar sizes and/or heights such that intra-operative adjustment of implant sizes can be accomplished. In some embodiments, the surgical tool may be fabricated onsite.

In some embodiments, the present system is employed with a method for a surgical procedure, which includes a step of determining an implant size using fluoroscopic imaging and/or physical measurement of disc space either pre-operative and/or intra-operative. In some embodiments, the method includes the step of determining and selecting a polymer substrate component with suitable footprint size and/or height. In some embodiments, the method includes the step of determining and selecting a pair of metal endplates with suitable footprint size and/or height. In some embodiments, the method includes the step of disposing one metal endplate on each side of the polymer substrate component in the surgical tool. In some embodiments, the method includes the step of aligning components and their corresponding attachment features. In some embodiments, the method includes the step of securing all components together for attachment. In some embodiments, the method includes the step of compressing the components to engage and/or attach the components by force, pressure, friction, heat, ultrasound, light and/or adhesive. In some embodiments, the method includes the step of sterilizing one and/or all of the components. In some embodiments, the method includes the step of determining and/or confirming proper implant size was selected. In some embodiments, the method includes the step of, if a non-desirable implant size was selected, disassembling the spinal implant and reassembling the spinal implant using suitable component sizes.

In some embodiments, the present system can be assembled on demand in a clinical and/or a sterile environment. In some embodiments, the present system can include personalized and/or customized spinal implants for assembly intra-operatively. In some embodiments, the present system includes solid titanium endplates, porous titanium endplates, chemically activated titanium endplates and/or HA-coated titanium endplates.

In some embodiments, the present system includes a set of assembly fixtures employed to align and protect the components of the present system during assembly using an assembly tool. In some embodiments, the assembly fixtures may be connected, attached, integrally assembled or monolithically formed with the assembly tool or separate from the assembly tool. In some embodiments, the assembly fixtures may have surfaces matching an endplate profile for maximum contact during assembly to reduce stress on the components of the present system. In some embodiments, the assembly fixtures may have surfaces made of materials to minimize wear or damage to the endplates during assembly. In some embodiments, the assembly fixtures may be made of plastic, composite or metallic materials such as polyethylene, PEEK, and stainless steel. In some embodiments, the assembly fixtures may be provided as sterile disposable or non-sterile reusable. In some embodiments, the assembly fixtures may be fabricated onsite using additive manufacturing, as described herein.

In some embodiments, the present system includes a personalized or custom spinal implant kit with predetermined footprint size and target height based on implant footprint size selected based on preference or pre-op planning, estimated implant height identified based on imaging diagnosis or pre-op planning, and/or components provided for a preselected footprint size and estimated height (+/−1 size in height).

In some embodiments, the present system includes a personalized or custom spinal implant kit with predetermined height and target footprint size based on implant height selected based on preference or pre-op planning, estimated implant footprint size identified based on imaging diagnosis or pre-op planning and/or components provided for the preselected height and estimated footprint size (+/−1 size in footprint if applicable).

In some embodiments, the present system includes a personalized or custom spinal implant kit with target footprint size and target height based on implant footprint size estimated based on preference or pre-op planning, estimated implant height identified based on imaging diagnosis or pre-op planning, and/or components provided for the estimated footprint size (+/−1 size in footprint if applicable) and the estimated height (+/−1 size in height).

In some embodiments, the present system includes a spinal implant kit with multiple material selections. For example, the spinal implant kit may have one or more endplates, for example, solid titanium, porous titanium, solid titanium-HA composite (porous titanium completely filled with HA) and/or porous titanium-coated with HA. In some embodiments, the present system spinal implant kit may have one or more substrates or middle components, for example, PEEK substrate, carbon-PEEK composite substrate, HA-PEEK substrate, polyethylene substrate and/or ceramic substrate.

In some embodiments, the present system includes personalized or custom spinal implants made by mixing and matching selected endplates and substrates. In some embodiments, the present system includes a personalized or custom spinal implant kit with preselected materials. For example, one or more endplates can be selected from solid titanium, porous titanium, solid titanium-HA composite (porous titanium completely filled with HA) and/or porous titanium-coated with HA and one or more substrates or middle components can be selected from PEEK substrate, carbon-PEEK composite substrate, HA-PEEK substrate, polyethylene substrate and/or ceramic substrate.

In some embodiments, the present system includes one or more spinal implants that can be assembled in a clinical setting. In some embodiments, the spinal implant includes an interbody device for PLIF, TLIF, DLIF, ACDF, OLIF and/or anterior lumbar interbody fusion (ALIF). In some embodiments, the spinal implant comprises a composite device with solid endplates, such as, for example, titanium including alloys and/or porous titanium filled with HA. In some embodiments, the spinal implant comprises a composite device with porous endplates, such as, for example, porous titanium including alloys and/or porous titanium coated with HA. In some embodiments, the endplate can include a porous titanium layer for bone ingrowth and a solid titanium layer for increased strength and mechanical properties for the overall endplate.

In some embodiments, the system includes endplates having various designs and ranges of dimensions. In some embodiments, the endplates can be substantially solid, substantially porous or partially porous with or without surface projection such as serration, teeth, ridges, spikes. In some embodiments, the endplates include a partial porous region and a solid region. In some embodiments, the regions can include various patterns or randomly distributed within the endplate, such as, for example, a bottom, top, front, back, side, uniformly or be randomly distributed, uniform or random pattern.

In some embodiments, the system includes an endplate having a thickness measurement extending from a bottom of the endplate to a tip of a tooth. In some embodiments, the thickness is between 0.1 millimeters (mm) to 5 mm. In some embodiments, the thickness is between 1 mm and 3 mm.

In some embodiments, the system includes an endplate having a partially porous configuration with a solid bottom layer for increased mechanical strength and a porous surface layer for bony tissue ingrowth. In some embodiments, the solid layer includes a thickness 0.1 mm and 3 mm. In some embodiments, the solid layer includes a thickness between 0.2 mm and 1 mm. In some embodiments, the porous layer includes thickness between 0.1 mm and 4 mm. In some embodiments, the porous layer includes a thickness between 0.2 mm and 3 mm including the teeth.

In some embodiments, the system includes endplates having a partially porous endplate with solid regions disposed on a top surface. In some embodiments, the porous regions must be at least 25% of the top surface layer. In some embodiments, the porous regions must be at least 50% of the top surface layer. In some embodiments, the porous regions must be at least 75% of the top surface layer.

In some embodiments, the porous portion includes an average pore size between 5 and 750 microns. In some embodiments, the porous portion includes an average pore size between 50 and 500 microns. In some embodiments, the solid portion includes a thickness between 25 microns and 1000 microns. In some embodiments, the solid portion includes a thickness between 50 and 500 microns. In some embodiments, the porosity can include various designs or patterns, such as, for example, an interconnected pore similar to trabecular bone.

In some embodiments, the endplates are assembled with a substrate by use of a surgical tool. In some embodiments, a force applied to assemble is between 0.01 Newtons (N) to 1000 N. In some embodiments, the force applied is between 0.1 N to 100 N. In some embodiments, the force applied to assemble is between 0.5 N to 50 N. In some embodiments, the force required depends on the attachment mechanism configured to provide a secure engagement while avoiding damage to the endplate surface features such as porosity, projections and/or osseoconductive coating.

In some embodiments, the system includes a single or multiple pieces with one embodiment of two mirror image fixture components matching the upper and lower endplates. In some embodiments, each component has an assembly tool-facing surface and implant facing surface. In some embodiments, the tool facing surface may have features for engaging and/or securing the fixture to a tool actuator or appropriate surface to apply force. In some embodiments, the implant facing surface may have a pocket or cavity that corresponds to the endplate and/or an endplate surface feature.

In some embodiments, the system includes components comprising materials, such as, for example, metals, polymers, ceramics or their composites configured for alignment, force transfer, implant surface protection from damage. In some embodiments, the materials may include, such as, for example, polyethylene, PEEK, 3D-printable polymers and/or stainless steel with polyethylene insert.

In some embodiments, the system includes an implant having holes or perforations configured to eject the implant from the surgical tool.

In some embodiments, the endplate is a substantially solid composite construct including of at least two different biomaterials. In some embodiments, the first biomaterial is a metallic material, such as, for example, titanium, titanium alloys including Nitinol, tantalum, Co—Cr and/or stainless steel. In some embodiments, the second biomaterial is a resorbable material or composite, such as, for example, HA, CP, tricalcium phosphate (TCP), HA-CP, HA-TCP, calcium sulfate, bioactive glasses, polylactic acid (PLA) polymer, polyglycolic acid (PGA) polymer, polylactic-glycolic acid (PLGA) copolymers, HA-PLA, HA-PGA, HA-PLGA, magnesium and/or HA-magnesium composite. In some embodiments, the biomaterials include, such as, for example, an osseoconductive for osseointegration.

In some embodiments, at least one of the biomaterials in the endplate is a continuous phase, such as, for example, the metallic material. In some embodiments, the endplate includes titanium having a plurality of holes or cavities such that the substantially non-connected holes or cavities are substantially filled with, such as, for example, HA, HA-TPC, HA-PLGA to form a substantially solid endplate.

In some embodiments, both biomaterials include a continuous phase having materials, such as, for example, heterogeneously mixed, each material being interconnected. In some embodiments, the endplate includes a three-dimensionally porous titanium endplate such that the substantially interconnected pores are substantially filled with material, such as, for example, HA, HA-TPC and/or HA-PLGA to form substantially solid endplates. In some embodiments, the second biomaterial may include other biological components, such as, for example, growth factors and/or pharmaceutical agents. In some embodiments, biological agents are added to the second biomaterial during manufacturing or in a clinical setting. In some embodiments, the endplate includes a three-dimensionally porous titanium endplate having substantially interconnected pores substantially filled with HA or HA-TPC that contains BMP2. In some embodiments, the endplate may include BMP2 incorporated into the second biomaterial by the manufacturer at manufacturing facility or by OR personnel during surgery, such as, for example, by soaking endplates in BMP2 solution for BMP2 absorption. In some embodiments, the second biomaterial is expected to resorb and be replaced by in-growing bone while the non-resorbable osseoconductive material is left behind to host bone ingrowth for long-term fixation.

In some embodiments, the endplates are fabricated using various conventional or special manufacturing methods, such as, for example, machining, additive manufacturing such as 3D printing and/or metal injection molding, for a first metallic phase and casting, insert molding and/or compression molding for the second resorbable phase. In some embodiments, the present system includes a spinal implant kit with biomaterial, mechanical sensors, electrical sensors, electrode, battery, power generator, microprocessor and/or a combination thereof, which may be attached to one or more spinal implants of the kit.

In some embodiments, the system includes a set of assembly fixtures configured for alignment of system components to protect the components during assembly using the assembly tool. In some embodiments, the fixture is configured for attachment with the assembly tool. In some embodiments, the fixture is separate from the assembly tool. In some embodiments, the fixtures may have surfaces matching the endplate profile for maximum contact during assembly in order to reduce stress. In some embodiments, the fixtures may have surfaces including materials configured to minimize wear and tear or damage to the endplates during assembly. In some embodiments, the fixtures include materials, such as, for example, plastic, composite or metallic materials such as polyethylene, PEEK and/or stainless steel. In some embodiments, the fixtures are provided as a sterile disposable or non-sterile reusable item. In some embodiments, the fixtures may be fabricated onsite using additive manufacturing, as described herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-7, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites, unless specifically referred to otherwise. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as PAEK including PEEK, PEKK and PEK, carbon-PEEK composites, PEEK-BaSO$_4$ polymeric rubbers, PET, fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as HA, corraline HA, biphasic calcium phosphate, fluorapatite, TCP, HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce surgical instrumentation, such as, for example, intra-operative surgical assembly tools and/or implants, such as, for example, an interbody implant, at a surgical site within a subject body of a patient, which includes, for example, a spine. In some embodiments, the implant can include spinal constructs including one or more bone fasteners, spinal rods, connectors and/or plates. In some embodiments, spinal implant system 10 includes one or a plurality of selected implants for a particular surgical procedure. In some embodiments, spinal implant system 10 includes one or a plurality of osseo-integration implants selectively personalized to a patient.

In some embodiments, spinal implant system 10 comprises a spinal implant kit, which includes one or a plurality of members that are connected via mating engagement for fixation of the members and assembly of a spinal implant, as described herein. In some embodiments, spinal implant system 10 comprises a spinal implant, such as, for example, an interbody implant 12. In some embodiments, interbody implant 12 includes a member, such as, for example, an endplate 14 and a member, such as, for example, an endplate 16. An intra-operative surgical tool, as described herein, is connected with endplate 14 and/or endplate 16 to engage adjacent mating elements of the members, as described herein. The intra-operative surgical tool compresses endplate 14 and/or endplate 16 with a member, such as, for example, an interbody substrate 18 for fixation of the members and assembly of interbody implant 12. In some embodiments, spinal implant system 10 comprises a spinal implant assembled of interchangeable members, as described herein. In some embodiments, spinal implant system 10 comprises a spinal implant that is selectively personalized or custom made to a patient for a particular surgical procedure by one or a plurality of combinations of selected endplates and/or selected interbody substrates.

In some embodiments, spinal implant system 10, which can include the spinal implant kits described herein, is employed with a method for on-site and/or intra-operative assembly of interbody implant 12 with members thereof being manufactured, fabricated or produced at locations, such as, for example, a manufacturers production facility, manufacturers global or local distribution center, hospital, outpatient surgery center and/or operating room. In some embodiments, the members can be manufactured, fabricated or produced via machining, molding, casting, sintering, and/or additive manufacturing such as 3D-printing or laser sintering. In some embodiments, endplates 14, 16 and interbody substrate 18 are fabricated at a hospital or an outpatient surgery center using additive manufacturing equipment such as 3D-printing or laser sintering on site. In some embodiments, the members of interbody implant 12 can be subjected to secondary preparation including trimming, machining, removing support materials, surface finishing, polishing, cleaning, decontamination and/or sterilization.

In some embodiments, the members of interbody implant 12 can be selected for a particular surgical procedure and/or from alternate members of a spinal implant kit, as described herein, based on one or more criteria. In some embodiments, the one or more criteria include, for example, anatomical parameters, implant parameters and/or surgical procedure parameters, as described herein. In some embodiments, the anatomical parameters can include condition, quality, configuration and/or dimension of selected anatomy, for example, one or more disc space dimensions, disc height, disc tissue, and/or one or more vertebra dimensions, vertebra/vertebrae height and/or vertebral tissue, and/or footprint associated with vertebral tissue including vertebrae and intervertebral discs. In some embodiments, the footprint can include the area defined by vertebral tissue, such as, for example, an endplate surface of one or more vertebra.

In some embodiments, the implant parameters can include predetermined and/or preselected implant size, predetermined and/or preselected implant height, predetermined and/or preselected footprint, targeted implant size, targeted implant height, targeted footprint and/or materials. In some embodiments, the surgical procedure parameters can include one or a plurality of vertebra, uni-lateral treatment, bi-lateral treatment, PLIF, TLIF, DLIF, ACDF, OLIF and/or ALIF.

In some embodiments, the members of interbody implant 12 can be selected prior to surgery. For example, a surgeon can conduct imaging diagnosis and/or pre-operative planning using medical imaging, as described herein, to measure anatomical parameters employed to determine implant parameters for selection of endplates 14, 16 and interbody substrate 18. In some embodiments, one or more members can be selected for assembly of a personalized interbody implant 12 with predetermined footprint size and target height based on implant footprint size. In some embodiments, one or more members can be selected for assembly of a personalized interbody implant 12 with predetermined height and target footprint size based on implant height selected. In some embodiments, one or more members can be selected for assembly of a personalized interbody implant 12 with target footprint size and target height based on implant footprint size estimated.

Endplate 14 extends between a vertebral engaging surface 20 and a surface 22. Surface 20 includes one or a plurality of tissue penetrating members, such as, for example, teeth 24. In one embodiment, one or more teeth 24 may have various configurations, for example, round, oval, rectangular, polygonal, irregular, tapered, offset, staggered, uniform and non-uniform. In some embodiments, surface 20 may be rough, textured, porous, semi-porous, dimpled, knurled, grooved and/or polished to facilitate engagement with tissue. In some embodiments, the vertebral tissue may include intervertebral tissue, endplate surfaces and/or cortical bone.

Surface 22 includes at least one mating element, such as, for example, pins 26 configured for mating engagement with interbody substrate 18, as described herein. Pins 26 are disposed in rows and equidistantly spaced along the length of endplate 14. In some embodiments, pins 26 are linearly aligned. In some embodiments, pins 26 extend perpendicular to surface 22. In some embodiments, pins 26 may be disposed at alternate orientations, relative to surface 22, such as, for example, transverse, and/or other angular orientations such as acute or obtuse, coaxial and/or may be offset or staggered. In some embodiments, surface 22 may include a mating element surface that can be rough, textured, porous, semi-porous, dimpled, knurled, toothed, grooved and/or polished to facilitate mating engagement with interbody substrate 18. In some embodiments, the mating element can include clips, key/keyslot, barbs, retaining tracks/slots and/or adhesive.

Pins 26 are configured for alignment and disposal with at least one mating element, such as, for example, pin slots 84 of interbody substrate 18. A surgical assembly tool compresses endplate 14 into mating engagement with interbody substrate 18 such that pins 26 are captured within slots 84 and endplate 14 is fixed with interbody substrate 18. In some embodiments, endplate 14 and interbody substrate 18 are compressed together such that pins 26 are disposed in a friction fit with the inner surface of slots 84 to fix endplate 14 with interbody substrate 18. In some embodiments, pin 26 includes an enlarged head or barb that is larger than slot 84 such that removal of pin 26 from slot 84 is resisted and/or prevented.

Figure 4:
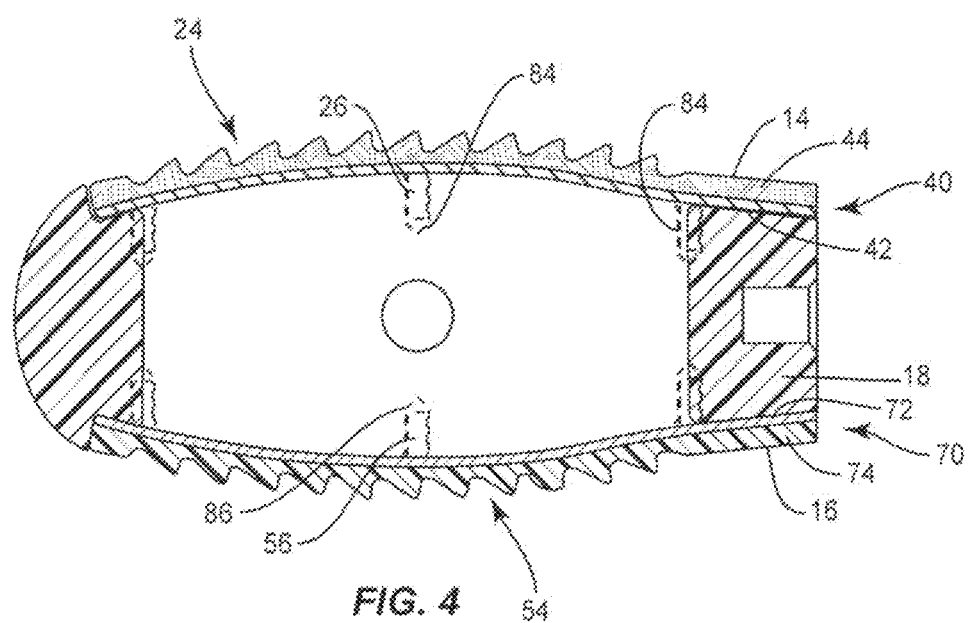
FIG. 4 is a side cross section view of the components shown in FIG. 1.

Endplate 14 includes a stratum 40 that extends between an end 30 and an end 32. End 30 is configured for engagement with a leading end 94 of interbody substrate 18, as described herein. End 32 is configured for engagement with an insertion end 96 of interbody substrate 18, as described herein. Stratum 40 includes a layer 42 and a layer 44, as shown in FIG. 4. Layer 42 includes a solid configuration that increases the strength of endplate 14. Layer 44 includes an interconnected porous configuration, which facilitates bone ingrowth. In some embodiments, stratum 40 includes one or a plurality of layers. In some embodiments, stratum 40 includes one or a plurality of layers, which may include solid titanium, porous titanium, solid titanium-HA composite (porous titanium completely filled with HA) and/or porous titanium-coated with HA.

Figure 7:
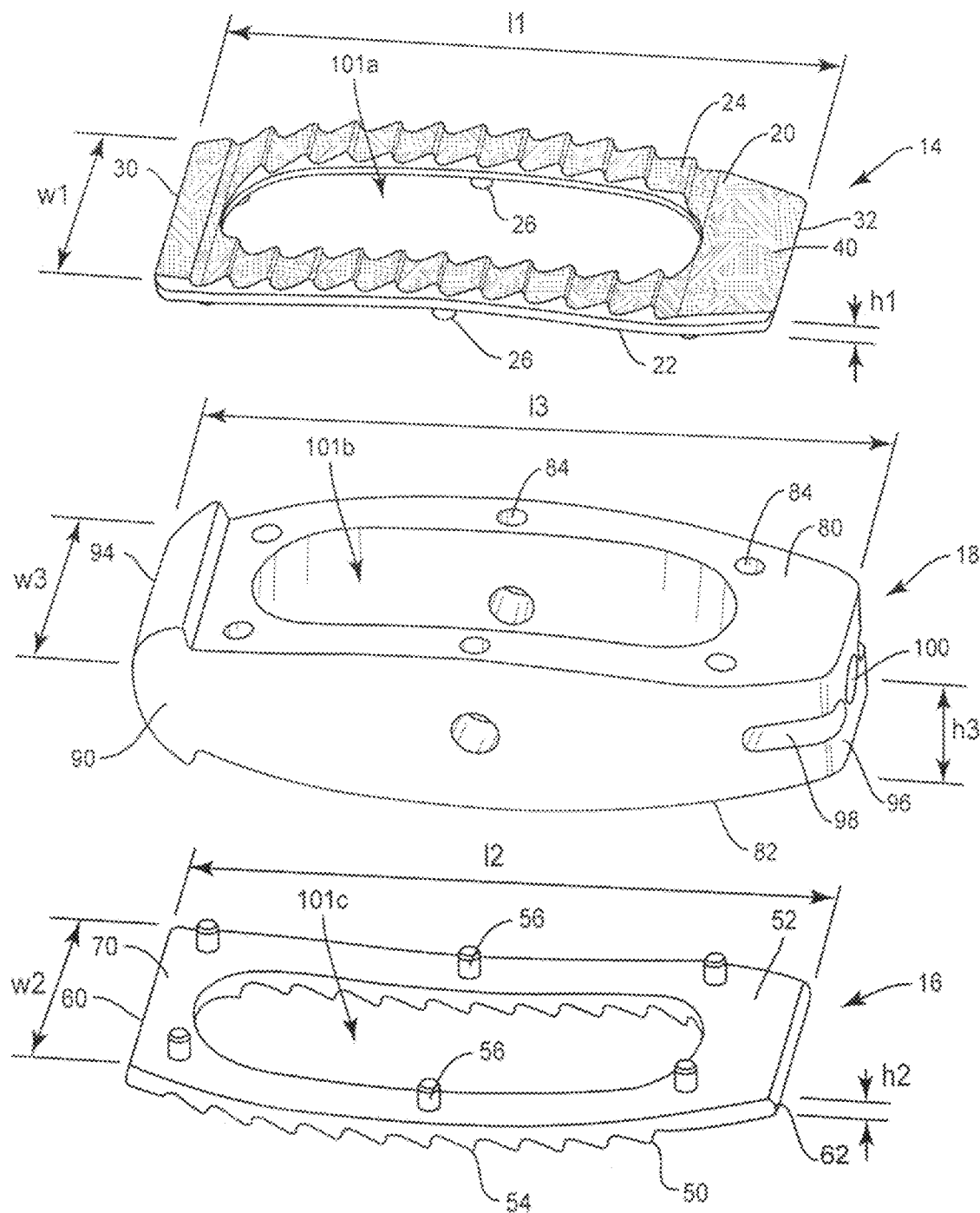
FIG. 7 is a perspective view of the components shown in FIG. 1 with parts separated.

Endplate 14 includes dimensions, such as, for example, a width w1, a thickness and/or height h1, and a length l1, as shown in FIG. 7. In some embodiments, endplate 14 and/or stratum 40 can be selected having selected dimensions from alternate endplates of the spinal implant kit based on one or more criteria, as described herein. In some embodiments, endplate 14 is configured for selection from a plurality of endplates of the spinal implant kit such that endplate 14 is interchangeable with interbody substrate 18. In some embodiments, one or more dimensions of endplate 14 are determined and selected based on a footprint of a selected anatomy, such as, for example, endplate surfaces of adjacent vertebrae having intervertebral disc tissue removed therebetween.

Endplate 16 extends between a vertebral engaging surface 50 and a surface 52. Surface 50 includes one or a plurality of tissue penetrating members, such as, for example, teeth 54. In one embodiment, one or more teeth 54 may have various configurations, for example, round, oval, rectangular, polygonal, irregular, tapered, offset, staggered, uniform and non-uniform. In some embodiments, surface 50 may be rough, textured, porous, semi-porous, dimpled, knurled, grooved and/or polished to facilitate engagement with tissue.

Surface 52 includes at least one mating element, such as, for example, pins 56 configured for mating engagement with interbody substrate 18, as described herein. Pins 56 are disposed in rows and equidistantly spaced along the length of endplate 16. In some embodiments, pins 56 are linearly aligned. In one embodiment, pins 56 extend perpendicular to surface 52. In some embodiments, pins 56 may be disposed at alternate orientations, relative to surface 52, such as, for example, transverse, and/or other angular orientations such as acute or obtuse, coaxial and/or may be offset or staggered. In some embodiments, surface 52 may include a mating element surface that can be rough, textured, porous, semi-porous, dimpled, knurled, toothed, grooved and/or polished to facilitate mating engagement with interbody substrate 18. In some embodiments, the mating element can include clips, key/keyslot, barbs, retaining tracks/slots, ridges, rivets, dovetail mechanism and/or adhesive.

Pins 56 are configured for alignment and disposal with at least one mating element, such as, for example, pin slots 86 of interbody substrate 18. A surgical assembly tool compresses endplate 16 into mating engagement with interbody substrate 18 such that pins 56 are captured within slots 86 and endplate 16 is fixed with interbody substrate 18. In some embodiments, endplate 16 and interbody substrate 18 are compressed together such that pins 56 are disposed in a friction fit with the inner surface of slots 86 to fix endplate 16 with interbody substrate 18. In some embodiments, pin 56 includes an enlarged head or barb that is larger than slot 86 such that removal of pin 56 from slot 86 is resisted and/or prevented.

Figure 5:
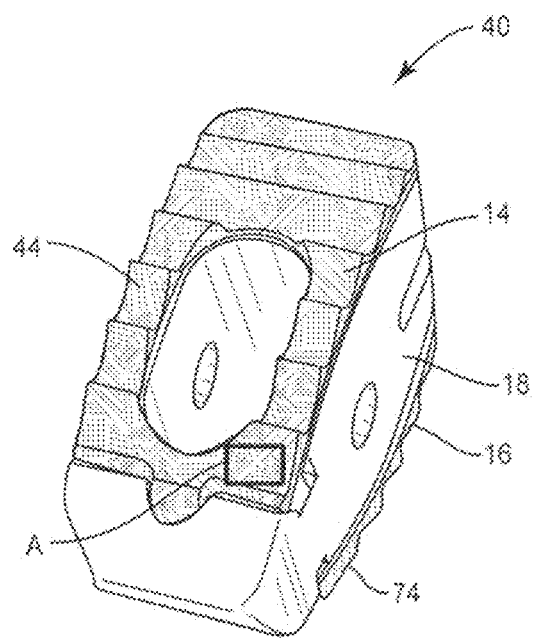
FIG. 5 is a perspective view of components of one embodiment of a surgical system in accordance with the principles of the present disclosure.
Figure 6:
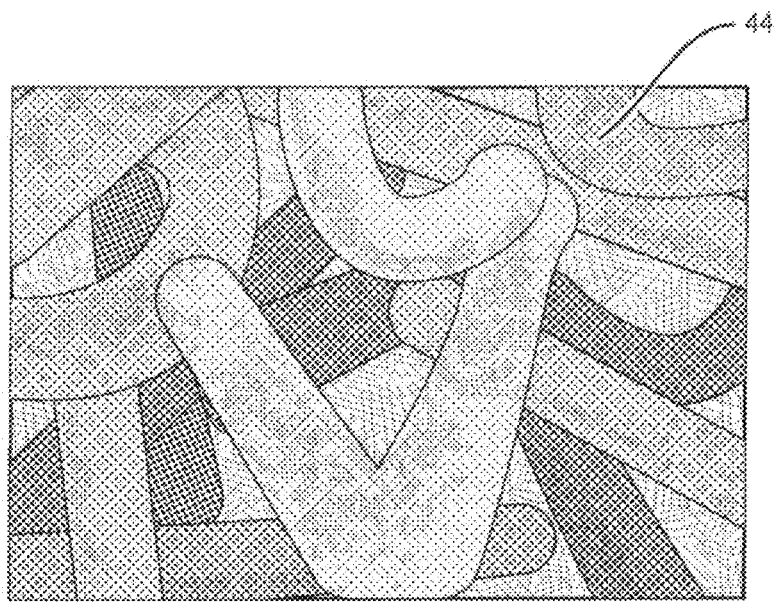
FIG. 6 is an enlarged view of detail A shown in FIG. 5.

Endplate 16 includes a stratum 70 that extends between an end 60 and an end 62. End 60 is configured for engagement with a leading end 94 of interbody substrate 18, as described herein. End 62 is configured for engagement with an insertion end 96 of interbody substrate 18, as described herein. Stratum 70 includes a layer 72 and a layer 74, as shown in FIG. 4. Layer 72 includes a solid configuration that increases the strength of endplate 16. Layer 74 includes a solid configuration. In some embodiments, stratum 70 includes one or a plurality of layers. In some embodiments, stratum 70 includes one or a plurality of layers, which may include solid titanium, porous titanium, solid titanium-HA composite (porous titanium completely filled with HA) and/or porous titanium-coated with HA. In some embodiments, as shown in FIGS. 5 and 6, layer 44 and layer 74 include an interconnected porous configuration, which facilitate bone ingrowth.

Endplate 16 includes dimensions, such as, for example, a width w2, a thickness and/or height h2, and a length l2. In some embodiments, endplate 16 and/or stratum 70 can be selected having selected dimensions from alternate endplates of the spinal implant kit based on one or more criteria, as described herein. In some embodiments, endplate 16 is configured for selection from a plurality of endplates of the spinal implant kit such that endplate 16 is interchangeable with interbody substrate 18. In some embodiments, one or more dimensions of endplate 16 are determined and selected based on a footprint of a selected anatomy, such as, for example, endplate surfaces of adjacent vertebrae having intervertebral disc tissue removed therebetween.

Interbody substrate 18 extends between a surface 80 and a surface 82. Surface 80 includes at least one mating element, such as, for example, slots 84. Slots 84 are configured for mating engagement with pins 26 to fix endplate 14 with interbody substrate 18, as described herein. In some embodiments, slots 84 extend perpendicular to surface 80. In some embodiments, slots 84 may be disposed at alternate orientations, relative to surface 80, such as, for example, transverse, and/or other angular orientations such as acute or obtuse, coaxial and/or may be offset or staggered.

Slots 84 are aligned to receive pins 26 for a mating engagement therebetween. A surgical assembly tool, as described herein, compresses endplate 14 into mating engagement with interbody substrate 18 such that pins 26 are captured within slots 84 and endplate 14 is fixed with interbody substrate 18. In some embodiments, surface 80 may include a mating element surface that can be rough, textured, porous, semi-porous, dimpled, knurled, toothed, grooved and/or polished to facilitate mating engagement with surface 22.

Surface 82 includes at least one mating element, such as, for example, slots 86. Slots 86 are configured for mating engagement with pins 56 to fix endplate 16 with interbody substrate 18, as described herein. In some embodiments, slots 86 extend perpendicular to surface 82. In some embodiments, slots 86 may be disposed at alternate orientations, relative to surface 82, such as, for example, transverse, and/or other angular orientations such as acute or obtuse, coaxial and/or may be offset or staggered.

Slots 84 are aligned to receive pins 56 for a mating engagement therebetween. A surgical assembly tool, as described herein, compresses endplate 16 into mating engagement with interbody substrate 18 such that pins 56 are captured within slots 86 and endplate 16 is fixed with interbody substrate 18. In some embodiments, surface 82 may include a mating element surface that can be rough, textured, porous, semi-porous, dimpled, knurled, toothed, grooved and/or polished to facilitate mating engagement with surface 52.

Interbody substrate 18 includes a stratum 90 that extends between an end, such as, for example, a leading end 94 and an end, such as, for example, an insertion end 96. End 94 includes a surface having a blunt tip to prevent interbody implant 12 from damaging surrounding tissue and/or nerves during insertion. End 96 includes a surface 98 that defines a cavity 100 configured for engagement with a surgical instrument, such as, for example, an insertion tool (not shown).

Interbody substrate 18 includes dimensions, such as, for example, a width w3, a thickness and/or height h3, and a length l3. In some embodiments, interbody substrate 18 and/or stratum 90 can be selected having selected dimensions from alternate substrates of the spinal implant kit based on one or more criteria, as described herein. In some embodiments, interbody substrate 18 is configured for selection from a plurality of interbody substrates of the spinal implant kit such that interbody substrate 18 is interchangeable with endplate 14 and/or endplate 16. In some embodiments, one or more dimensions of interbody substrate 18 are determined and selected based on a footprint of a selected anatomy, such as, for example, endplate surfaces of adjacent vertebrae having intervertebral disc tissue removed therebetween.

In some embodiments, the cross-section geometry of interbody implant 12 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, interbody implant 12 includes an opening 101, which includes an opening 101a of endplate 14, an opening 101b of interbody substrate 18 and an opening 101c of endplate 16, configured to receive an agent, which may include bone graft (not shown) and/or other materials, as described herein, for employment in a fixation or fusion treatment, as described herein. In one embodiment, the agent may include therapeutic polynucleotides or polypeptides and bone growth promoting material, which can be packed or otherwise disposed on or about the surfaces of the components of spinal implant system 10, including interbody implant 12. In some embodiments, the spinal implant kit is provided with sterile-packed components to form interbody implant 12. In some embodiments, some of the components of the spinal implant kit are sterilized and configured for sterilization in the operating room. In some embodiments, all of the components of the spinal implant kit are configured for sterilization after interbody implant 12 is formed.

Figure 8:
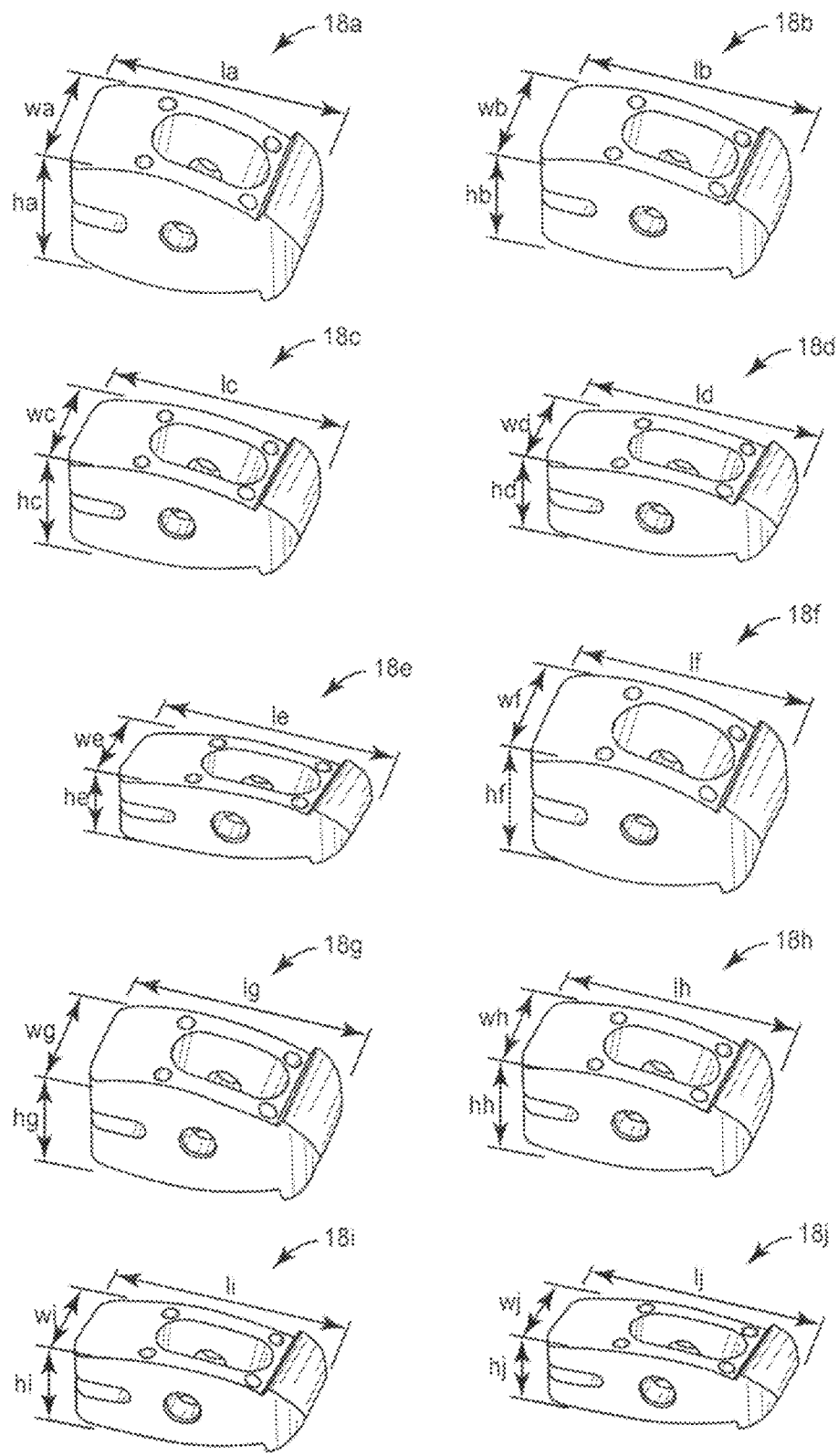
FIG. 8 is a perspective view of components of one embodiment of a surgical system in accordance with the principles of the present disclosure.
Figure 9:
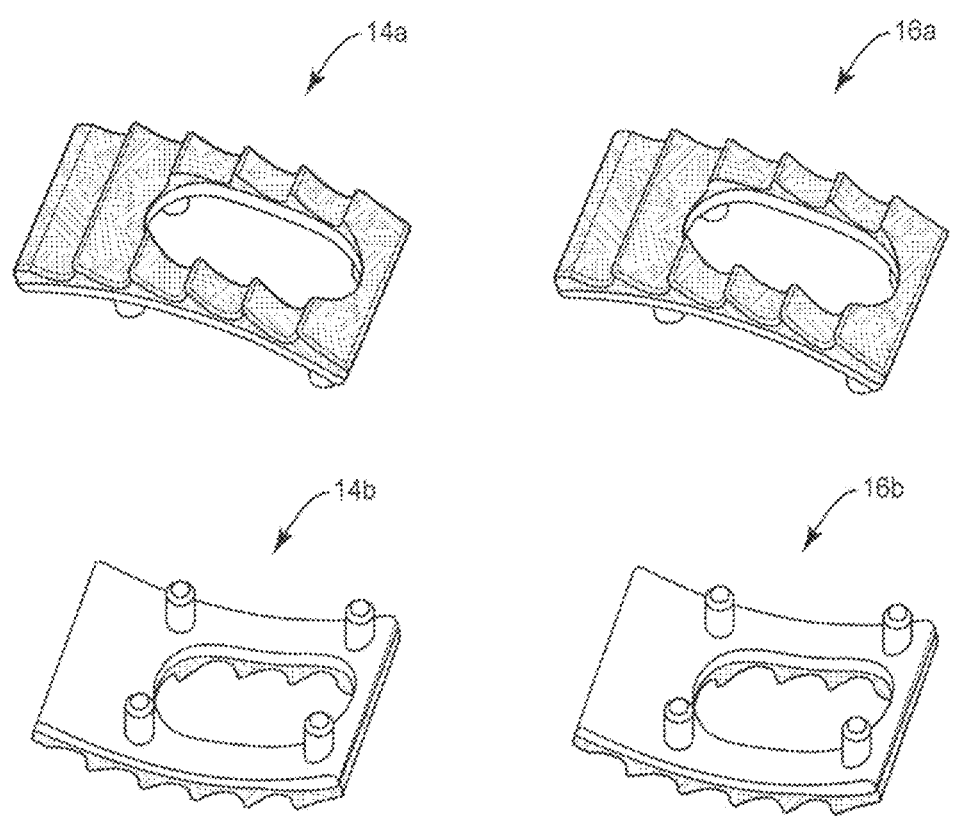
FIG. 9 is a perspective view of components of one embodiment of a surgical system in accordance with the principles of the present disclosure.

In some embodiments, the spinal implant kit includes a plurality of interbody substrates 18 having various sizes, such as, for example, interbody substrates 18a-18j having different sized widths wa-wj, thickness and/or height ha-hj, and lengths la-lj, as shown in FIG. 8. As such, interbody substrate 18 is selected from a plurality of interbody substrates 18a-18j provided in spinal implant kit and intra-operatively assembled with endplates 14, 16, as described herein. Interbody implant 12 includes a footprint having a height H, width W and length L, as described herein. In some embodiments, height H is equal to h1+h2+h3. In some embodiments, width W is equal to the greater of w1, w2 and w3. In some embodiments, length L is equal to the greater of l1, l2 and l3. In some embodiments, the spinal implant kit includes a plurality of alternate endplates, which include endplates 14, 16 described herein, and at least endplates 14a, 16a and endplates 14b, 16b, as shown in FIG. 9. Endplates 14, 14a, 14b, 16, 16a and/or 16b are alternately sized and/or configured relative to one or more dimensions, as described herein.

Figure 10:
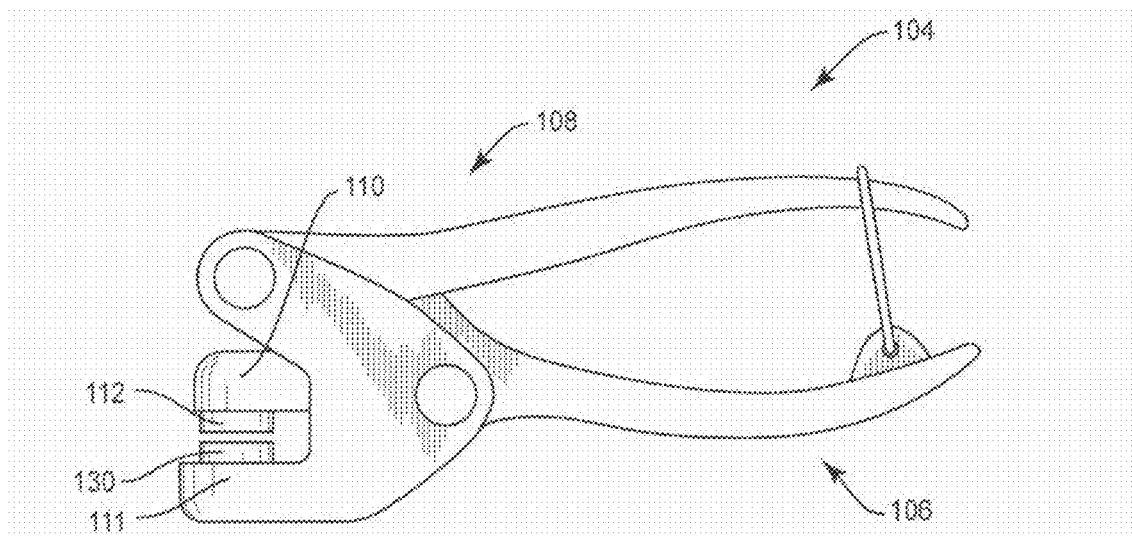
FIG. 10 is a perspective view of components of one embodiment of a surgical system in accordance with the principles of the present disclosure.
Figure 11:
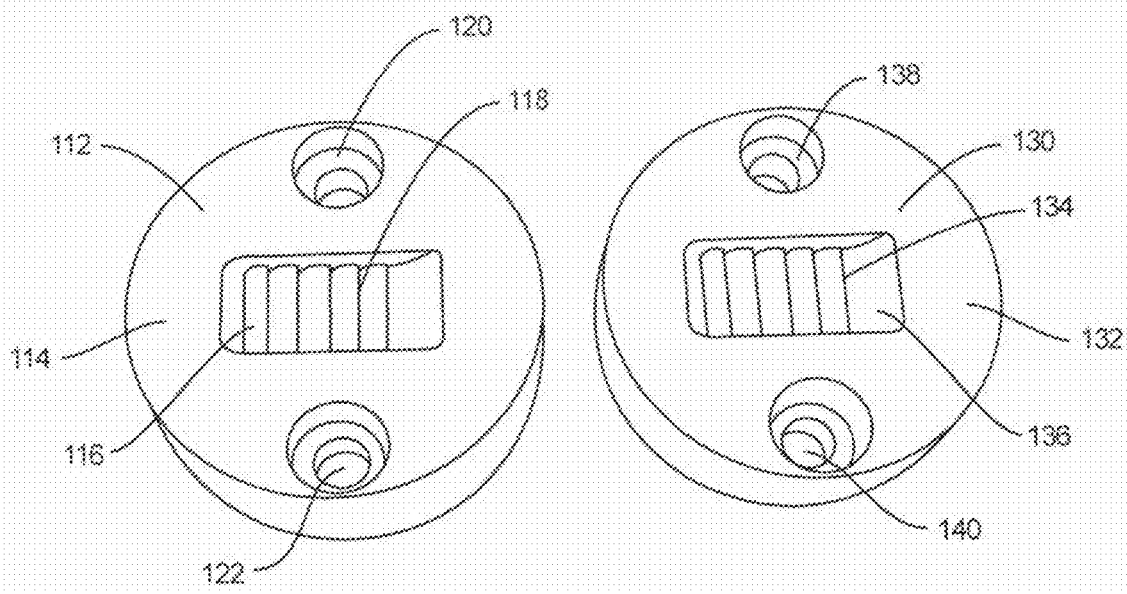
FIG. 11 is a perspective view of components of one embodiment of a surgical system in accordance with the principles of the present disclosure.

In one embodiment, as shown in FIGS. 10 and 11, spinal implant system 10 includes an intra-operative surgical assembly tool, such as, for example, a hand press 104. Hand press 104, as described herein, is connected with members, such as, for example, endplate 14 and/or endplate 16 to engage adjacent mating elements of the members, as described herein. Hand press 104 compresses endplate 14 and/or endplate 16 with a member, such as, for example, interbody substrate 18 for fixation of the members and assembly of a spinal implant, such as, for example, interbody implant 12. In some embodiments, hand press 104 attaches endplates 14, 16 with interbody substrate 18 by attachment of both endplates 14, 16 to interbody substrate 18 simultaneously. In some embodiments, hand press 104 attaches endplates 14, 16 with interbody substrate 18 by attachment of endplate 14 to interbody substrate 18 and subsequent attachment of endplate 16 to interbody substrate 18. In some embodiments, the spinal implant kit includes hand press 104.

Hand press 104 includes a handle 106 connected with an actuator 108. Handle 106 is manipulated to actuate relatively movable jaws 110, 111 of actuator. Jaws 110, 111 engage and align endplates 14, 16 and/or interbody substrate 18 to apply force and/or pressure such that endplates 14, 16 are assembled with interbody substrate 18. In some embodiments, handle 106 provides a practitioner leverage to apply pressure to the members of interbody implant 12 to facilitate assembly thereof. In some embodiments, hand press 104 includes indicia and/or an indicator, such as, for example, graduated markings, a meter or gauge to display force stress. In some embodiments, hand press 104 includes heating, cooling, ultrasonic welding, disassembly, manual or power/automatic operation of one or more operations in connection with the present systems and methods for assembling a spinal implant. In some embodiments, hand press 104 is adjustable to accommodate various implant sizes, alternately interchangeable inserts to accommodate different sizes of implant in footprint, angulation and/or height variations.

Jaw 110 includes an engagement part 112 having a surface 114 that defines a cavity, such as, for example, a slot 116. Slot 116 is configured for disposal and capture of endplate 14, endplate 16 and/or interbody substrate 18. In some embodiments, slot 116 is configured for disposal and capture of one or a plurality of members, as described herein. In some embodiments, surface 114 includes a mating element or surface that matches an endplate or substrate profile for contact with surfaces of endplates 14, 16, such as, for example, surfaces 20, 50 during assembly of interbody implant 12. For example, surface 114 includes grooves 118 that match the configuration of teeth 24 and the profile of surface 20. In some embodiments, this configuration reduces stress on the members of interbody implant 12. Part 112 includes countersunk holes 120, 122 for mounting part 112 to jaw 110 via fasteners (not shown).

Jaw 111 includes an engagement part 130 having a surface 132 that defines a cavity, such as, for example, a slot 134. Slot 134 is configured for disposal and capture of endplate 14, endplate 16 and/or interbody substrate 18. In some embodiments, slot 134 is configured for disposal and capture of one or a plurality of members, as described herein. In some embodiments, surface 134 includes a mating element or surface that matches an endplate or substrate profile for contact with surfaces of endplates 14, 16, such as, for example, surfaces 20, 50 during assembly of interbody implant 12. For example, surface 132 includes grooves 136 that match the configuration of teeth 54 and the profile of surface 50. In some embodiments, this configuration reduces stress on the members of interbody implant 12. Part 130 includes countersunk holes 138, 140 for mounting part 130 to jaw 111 via fasteners (not shown).

Slots 116, 134 capture the members of interbody implant 12 such that parts 112, 130 are disposed with actuator 108 to align and guide endplate 14, endplate 16 and interbody substrate 18 in assembly with hand press 104. Parts 112, 130 compress towards each other to apply a force and/or pressure to the members of interbody implant 12 for assembly thereof. This configuration protects the members of interbody implant 12 during assembly.

In some embodiments, surfaces 114, 132 are fabricated from materials to minimize wear or damage to the members of interbody implant 12 during assembly. In some embodiments, parts 112, 130 are fabricated from plastic, composite or metallic materials such as polyethylene, PEEK, and stainless steel. In some embodiments, parts 112, 130 are provided as sterile disposable or non-sterile reusable. In some embodiments, parts 112, 130 are fabricated on-site using additive manufacturing, as described herein. In some embodiments, parts 112, 130 may be connected, attached, integrally assembled or monolithically formed with hand press 104. In some embodiments, part 112 and/or part 130 are separate and mounted with hand press 104. In some embodiments, part 112 and/or part 130 includes one or more cavities, slots, ridges, pins, guides and/or tabs for capture of one or more members.

In some embodiments, hand press 104 assembles one or more spinal implants, as described herein, prior to or during a surgical procedure inside or outside a clinical setting. In some embodiments, hand press 104 is sterilized and re-sterilized in a clinical setting. In some embodiments, hand press 104 is provided as a sterile disposable item. In some embodiments, hand press 104 disassembles interbody implant 12. In some embodiments, hand press 104 is provided in a non-sterile package and is compatible with sterilization process in clinical settings. In some embodiments, hand press 104 can be made of metal, polymer, ceramic, composite or their combinations. In some embodiments, hand press 104 may be manually operated or electrically powered. In some embodiments, hand press 104 is programmable and automated. In some embodiments, hand press 104 assembles one or more spinal implants, as described herein, on demand in a clinical and/or a sterile environment. In some embodiments, hand press 104 assembles personalized and/or customized spinal implants for assembly intra-operatively.

Figure 12:
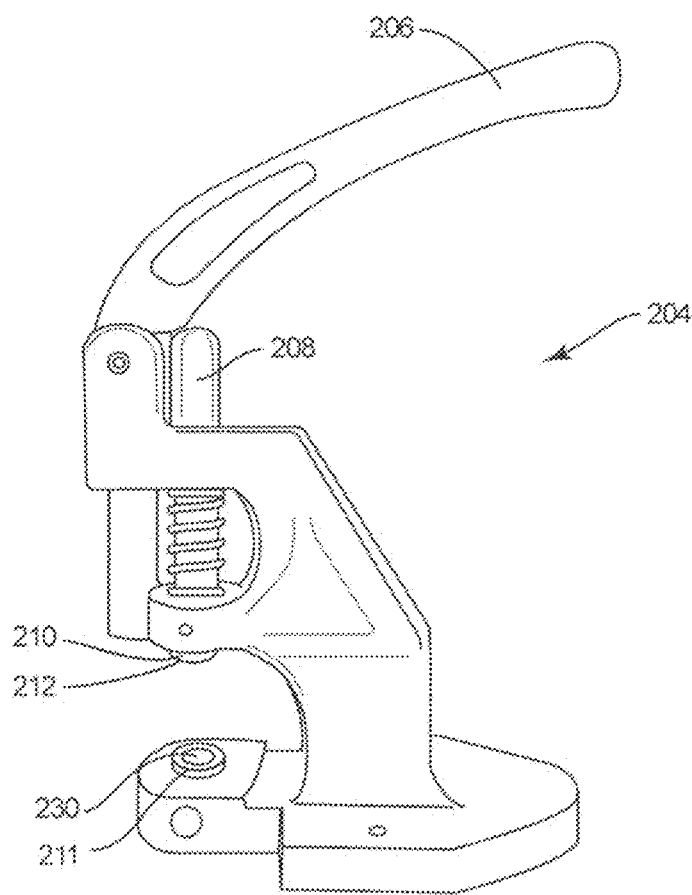
FIG. 12 is a perspective view of components of one embodiment of a surgical system in accordance with the principles of the present disclosure.

In one embodiment, as shown in FIG. 12, spinal implant system 10 includes an intra-operative surgical assembly tool, such as, for example, a table top hand press 204, similar to hand press 104 described with regard to FIGS. 10 and 11. Hand press 204 is connected with members, such as, for example, endplate 14 and/or endplate 16 to engage adjacent mating elements of the members, as described herein. Hand press 204 compresses endplate 14 and/or endplate 16 with a member, such as, for example, interbody substrate 18 for fixation of the members and assembly of a spinal implant, such as, for example, interbody implant 12, similar to that described herein.

Hand press 204 includes a handle 206 connected with an actuator 208 having jaws 210, 211, similar to jaws 110, 111 described herein. Jaw 210 includes an engagement part 212, similar to part 112 described herein. Jaw 211 includes an engagement part 230, similar to part 112 described herein. Parts 212, 230 capture the members of interbody implant 12 such that parts 212, 230 align and guide endplate 14, endplate 16 and interbody substrate 18 in assembly with hand press 204, similar to that described with regard to hand press 104.

Figure 13:
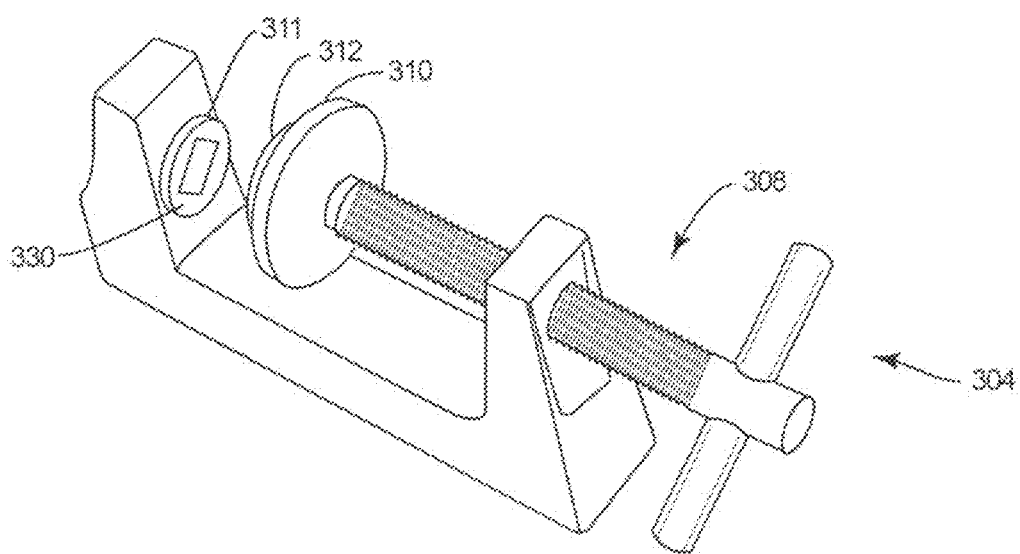
FIG. 13 is a perspective view of components of one embodiment of a surgical system in accordance with the principles of the present disclosure.

In one embodiment, as shown in FIG. 13, spinal implant system 10 includes an intra-operative surgical assembly tool, such as, for example, a vise 304, similar to hand press 104 described with regard to FIGS. 10 and 11. Vise 304 is connected with members, such as, for example, endplate 14 and/or endplate 16 to engage adjacent mating elements of the members, as described herein. Hand press 304 compresses endplate 14 and/or endplate 16 with a member, such as, for example, interbody substrate 18 for fixation of the members and assembly of a spinal implant, such as, for example, interbody implant 12, similar to that described herein.

Vise 304 includes an actuator 308 having jaws 310, 311, similar to jaws 110, 111 described herein. Jaw 310 includes an engagement part 312, similar to part 112 described herein. Jaw 311 includes an engagement part 330, similar to part 112 described herein. Parts 312, 330 capture the members of interbody implant 12 such that parts 312, 330 align and guide endplate 14, endplate 16 and interbody substrate 18 in assembly with vise 304, similar to that described with regard to hand press 104.

Figure 14:
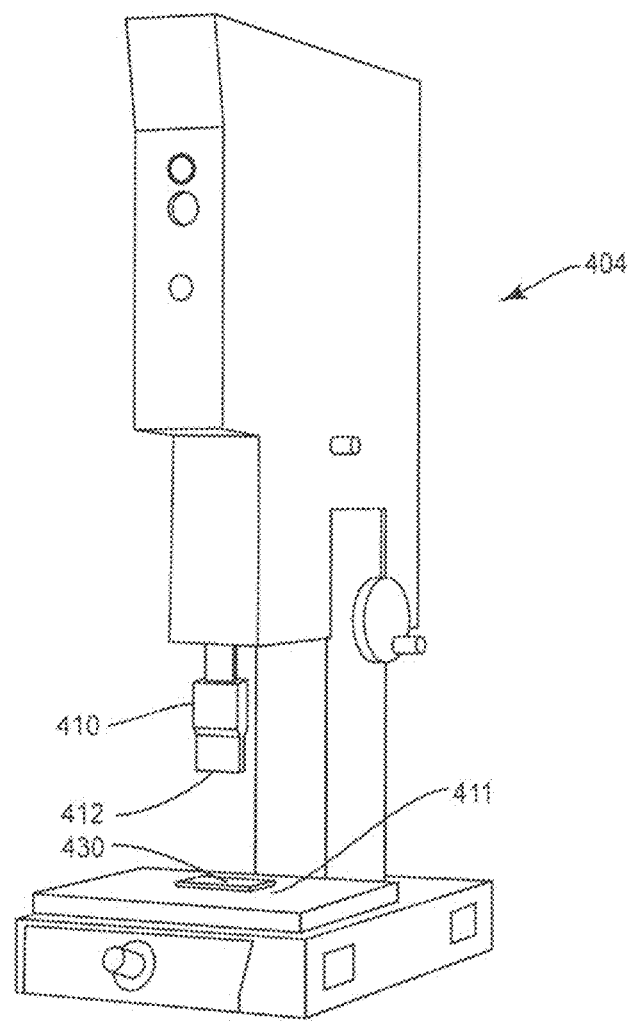
FIG. 14 is a perspective view of components of one embodiment of a surgical system in accordance with the principles of the present disclosure.

In one embodiment, as shown in FIG. 14, spinal implant system 10 includes an intra-operative surgical assembly tool, such as, for example, an ultrasonic welding press 404, similar to hand press 104 described with regard to FIGS. 10 and 11. Ultrasonic welding press 404 is connected with members, such as, for example, endplate 14 and/or endplate 16 to engage adjacent mating elements of the members, as described herein. Ultrasonic welding press 404 compresses endplate 14 and/or endplate 16 with a member, such as, for example, interbody substrate 18 for fixation of the members and assembly of a spinal implant, such as, for example, interbody implant 12, similar to that described herein.

Ultrasonic welding press 404 includes jaws 410, 411, similar to jaws 110, 111 described herein. Jaw 410 includes an engagement part 412, similar to part 112 described herein. Jaw 411 includes an engagement part 430, similar to part 112 described herein. Parts 412, 430 capture the members of interbody implant 12 such that parts 412, 430 align and guide endplate 14, endplate 16 and interbody substrate 18 in assembly with ultrasonic welding press 404, similar to that described with regard to hand press 104. Ultrasonic welding press 404 applies high-frequency ultrasonic acoustic vibrations to the members of interbody implant 12 being held with parts 412, 430 under pressure to create a solid-state weld.

Figure 15:
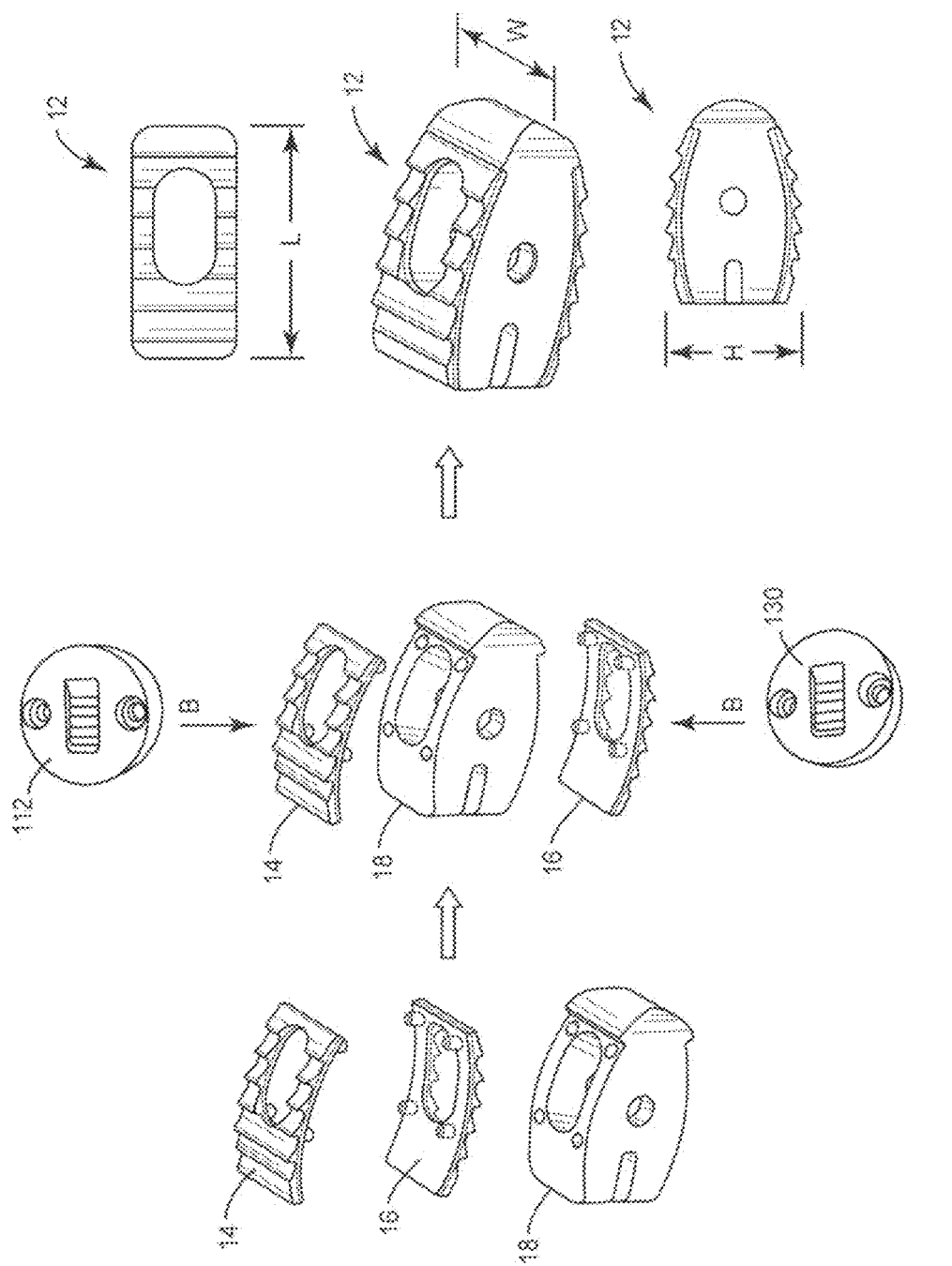
FIG. 15 is a schematic view of components of one embodiment of a surgical system in accordance with the principles of the present disclosure.
Figure 16:
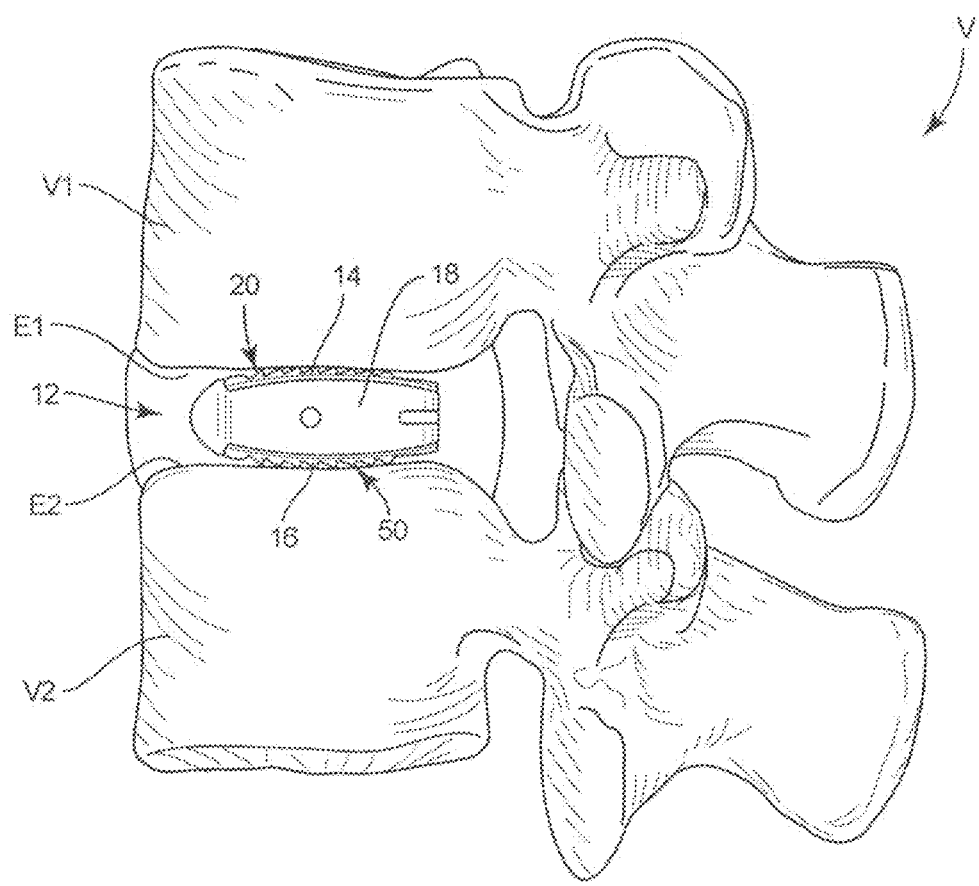
FIG. 16 is a side view of components of one embodiment of a surgical system in accordance with the principles of the present disclosure disposed with vertebrae.

In assembly, operation and use, as shown in FIGS. 15 and 16, spinal implant system 10, similar to the systems and methods described herein, is disposed with tissue, such as, for example, vertebrae V for treatment of a spinal disorder, such as those described herein, affecting a section of a spine of a patient. Spinal implant system 10 may also be employed with other surgical procedures.

In some embodiments, spinal implant system 10 including the spinal implant kits described herein is employed with a method for intra-operatively assembly of interbody implant 12 with endplates 14, 16 and interbody substrate 18 being manufactured, fabricated or produced at locations, such as, for example, a manufacturers production facilities, manufacturers global or local distribution centers, hospitals, outpatient surgery centers and/or operating rooms. In some embodiments, the members can be manufactured, fabricated or produced via machining, molding, casting, sintering, and/or additive manufacturing such as 3D-printing or laser sintering. In some embodiments, endplates 14, 16 and interbody substrate 18 are fabricated at a hospital or an outpatient surgery center using additive manufacturing equipment such as 3D-printing or laser sintering on site. In some embodiments, endplates 14, 16 and interbody substrate 18 can be subjected to secondary preparation including trimming, machining, removing support materials, surface finishing, polishing, cleaning, decontamination and/or sterilization.

In some embodiments, endplates 14, 16 and/or interbody substrate 18 can be selected for a particular surgical procedure using criteria, such as, for example, an interbody implant 12 footprint having a height H, length L and width W, as described herein. Interbody implant 12 is assembled to conform to a determined footprint of an intervertebral space. In some embodiments, the surgical procedure parameters can include one or a plurality of vertebra, uni-lateral treatment, bi-lateral treatment, PLIF, TLIF, DLIF, ACDF, OLIF and/or ALIF.

In some embodiments, the members of interbody implant 12 can be selected prior to surgery. For example, a surgeon can conduct imaging diagnosis and/or pre-operative planning using medical imaging, as described herein, to measure anatomical parameters employed to determine interbody implant 12 parameters for selection of endplates 14, 16 and interbody substrate 18. In some embodiments, one or more endplates 14, 16 and/or interbody substrate 18 can be selected for assembly intra-operatively from the spinal implant kit for a personalized interbody implant 12.

To treat the affected section of vertebrae V, such as, for example, vertebrae V1, V2, an incision is made with a surgical instrument, such as, for example, a scalpel. In some embodiments, a discectomy is performed adjacent the intervertebral space between an endplate E1 and an endplate E2. In some embodiments, sequential trial implants are delivered and used to distract the intervertebral space and apply appropriate tension in the intervertebral space allowing for indirect decompression. In some embodiments, the footprint of interbody implant 12 is selected after trialing.

In some embodiments, spinal implant system 10 includes a spinal implant kit having a plurality of alternate endplates 14, 16 that are interchangeable with a plurality of interbody substrates 18, as described herein. Endplates 14, 16 and interbody substrate 18 are selected for assembly of a personalized interbody implant 12 with a predetermined footprint size having a width W, height H and length L, as shown in FIG. 15 and described herein. For example, pins 26 of endplate 14 are aligned with slots 84 of interbody substrate 18 for fixation of the members of interbody implant 12. Pins 56 of endplate 16 are aligned with slots 86 of interbody substrate 18 for fixation of the members of interbody implant 12.

A surgical assembly tool, as described herein, is intra-operatively connected with endplate 14 and endplate 16 to engage adjacent mating elements of endplates 14, 16 and interbody substrate 18 to assemble endplates 14, 16 with interbody substrate 18. Part 112 of a surgical assembly tool, as shown in FIG. 15 and described herein, captures endplate 14 and part 130 captures endplate 16. The surgical assembly tool applies a compressive force, as shown by arrows B in FIG. 15, to endplates 14, 16 and interbody substrate 18 to fix pins 26 with slots 84 and fix pins 56 with slots 86 to assemble interbody implant 12.

An inserter (not shown) is connected with interbody implant 12 to direct interbody implant 12 between vertebrae V1, V2 such that surface 20 is disposed with endplate E1 and surface 50 is disposed with endplate E2. The inserter delivers interbody implant 12 through the incision to the surgical site for implantation into the intervertebral space between vertebrae V1, V2 such that interbody implant 12 is disposed with vertebrae V1, V2, as shown in FIG. 16, for treatment of a spinal disorder. In some embodiments, interbody implant 12 is visualized by fluoroscopy and oriented before malleting into the intervertebral space.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT, MRI or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method comprising:
disposing a first endplate in a first jaw of a surgical tool and disposing a second endplate in a second jaw of the surgical tool;
positioning a substrate between the endplates; and
manipulating the surgical tool to move the first jaw toward the second jaw such that pins of the endplates move into slots in the substrate to couple the endplates to the substrate,
wherein disposing the first endplate in the first jaw comprises disposing an entire perimeter of the first endplate in a recess in the first jaw, and
wherein the first endplate comprises a first surface having teeth and an opposite second surface, the first jaw comprising grooves that match a configuration of the teeth.

2. A method as recited in claim 1, wherein the pins of the first endplate move into slots in a proximal surface of the substrate and the pins of the second endplate move into slots in an opposite distal surface of the substrate as the first jaw moves toward the second jaw.

3. A method as recited in claim 1, wherein the recess extends into the first surface of the first jaw without extending through the second surface of the first jaw.

4. A method as recited in claim 1, wherein the pins of the first endplate extend outwardly from the second surface, the pins of the first endplate moving into slots in the substrate as the first jaw moves toward the second jaw.

5. A method as recited in claim 1, wherein disposing the second endplate in the second jaw comprises disposing an entire perimeter of the second endplate in a second recess in the second jaw.

6. A method as recited in claim 5, wherein the second recess extends into a first surface of the second jaw without extending through an opposite second surface of the second jaw.

7. A method as recited in claim 5, wherein the second endplate comprises a first surface having teeth and an opposite second surface, the second recesses comprising grooves that match a configuration of the teeth of the second endplate.

8. A method as recited in claim 7, wherein the pins of the first endplate extend outwardly from the second surface of the first endplate and the pins of the second endplate extend outwardly from the second surface of the second endplate, the pins of the first endplate moving into slots in a proximal surface of the substrate as the first jaw moves toward the second jaw and the pins of the second endplate moving into slots in an opposite distal surface of the substrate as the first jaw moves toward the second jaw.

9. A method comprising:
disposing a first endplate in a first jaw of a surgical tool and disposing a second endplate in a second jaw of the surgical tool;
positioning a substrate between the endplates; and
manipulating the surgical tool to move the first jaw toward the second jaw such that pins of the endplates move into slots in the substrate to couple the endplates to the substrate,
wherein disposing the first endplate in the first jaw comprises disposing an entire perimeter of the first endplate in a first recess in the first jaw and disposing the second endplate in the second jaw comprises disposing an entire perimeter of the second endplate in a second recess in the second jaw, and
wherein the first endplate comprises a first surface having teeth and an opposite second surface, the second endplate comprising a first surface having teeth and an opposite second surface, the first recess comprising grooves that match a configuration of the teeth of the first endplate and the second recesses comprises grooves that match a configuration of the teeth of the second endplate.

10. A method as recited in claim 9, wherein the first recess extends into the first surface of the first jaw without extending through the second surface of the first jaw and the second recess extends into the first surface of the second jaw without extending through the second surface of the second jaw.

11. A method as recited in claim 9, wherein the pins of the first endplate move into slots in a proximal surface of the substrate and the pins of the second endplate move into slots in an opposite distal surface of the substrate as the first jaw moves toward the second jaw.

12. A method as recited in claim 9, wherein the pins of the first endplate extend outwardly from the second surface of the first endplate, the pins of the first endplate moving into slots in the substrate as the first jaw moves toward the second jaw.

13. A method as recited in claim 9, wherein the pins of the second endplate extend outwardly from the second surface of the second endplate, the pins of the second endplate moving into slots in the substrate as the first jaw moves toward the second jaw.

14. A method comprising:
disposing a first endplate in a first jaw of a surgical tool and disposing a second endplate in a second jaw of the surgical tool;
positioning a substrate between the endplates; and
manipulating the surgical tool to move the first jaw toward the second jaw such that pins of the endplates move into slots in the substrate to couple the endplates to the substrate,
wherein disposing the first endplate in the first jaw comprises disposing an entire perimeter of the first endplate in a first recess in the first jaw and disposing the second endplate in the second jaw comprises disposing an entire perimeter of the second endplate in a second recess in the second jaw, wherein the first endplate comprises a first surface having teeth and an opposite second surface, the second endplate comprising a first surface having teeth and an opposite second surface, the first recess comprising grooves that match a configuration of the teeth of the first endplate and the second recesses comprises grooves that match a configuration of the teeth of the second endplate, and the pins of the first endplate extend outwardly from the second surface of the first endplate and the pins of the second endplate extend outwardly from the second surface of the second endplate, the pins of the first endplate moving into slots in a proximal surface of the substrate as the first jaw moves toward the second jaw and the pins of the second endplate moving into slots in an opposite distal surface of the substrate as the first jaw moves toward the second jaw.

15. A method as recited in claim 14, wherein the first recess extends into the first surface of the first jaw without extending through the second surface of the first jaw and the second recess extends into the first surface of the second jaw without extending through the second surface of the second jaw.

16. A method as recited in claim 14, wherein the pins of the first endplate move into slots in a proximal surface of the substrate and the pins of the second endplate move into slots in an opposite distal surface of the substrate as the first jaw moves toward the second jaw.

\* \* \* \* \*